US006971261B2

(12) United States Patent
Ischdonat et al.

(10) Patent No.: US 6,971,261 B2
(45) Date of Patent: Dec. 6, 2005

(54) METHOD AND APPARATUS FOR DETERMINING AT LEAST ONE PROPERTY OF MOVING CLOTHING IN A PAPER MACHINE

(75) Inventors: Thomas Ischdonat, Bachhagel (DE); Ralf Pfifferling, Gerstetten (DE); Rudolf Muench, Koenigsbronn (DE); Michael Sollinger, Stuttgart (DE)

(73) Assignee: Voith Paper Patent GmbH, Heidenheim (DE)

( * ) Notice: Subject to any disclaimer, the term of this patent is extended or adjusted under 35 U.S.C. 154(b) by 0 days.

(21) Appl. No.: 10/943,656

(22) Filed: Sep. 17, 2004

(65) Prior Publication Data
US 2005/0145043 A1   Jul. 7, 2005

(30) Foreign Application Priority Data
Sep. 19, 2003   (DE) .................... 103 43 516

(51) Int. Cl.[7] ............................... G01D 5/44
(52) U.S. Cl. ................ 73/38; 162/198; 162/263
(58) Field of Search .............. 73/38, 159; 162/49, 162/198, 263

(56) References Cited

U.S. PATENT DOCUMENTS

| 4,880,499 A | * | 11/1989 | Pikulik ..................... 162/198 |
| 5,725,737 A | * | 3/1998 | Pikulik et al. .............. 162/263 |
| 6,266,999 B1 | * | 7/2001 | Arnshav ..................... 73/38 |

* cited by examiner

*Primary Examiner*—Hezron Williams
*Assistant Examiner*—Paul M. West
(74) *Attorney, Agent, or Firm*—Taylor & Aust, P.C.

(57) ABSTRACT

A method of determining at least one property of moving clothing of a machine for producing and/or treating a material web, in particular a paper or board web, which includes the following steps: arranging a nozzle opposite the surface of the moving clothing; producing a jet acting on the clothing by way of the nozzle contacting the moving clothing; measuring a variable representative of the flow through the nozzle; measuring a variable representative of the pressure of the jet at the nozzle outlet; determining the speed of the jet at the nozzle outlet from the nozzle flow and the free surface of the jet medium at the point of contact with the clothing; and determining the speed of the jet at the entry into the clothing from the speed of the jet at the nozzle outlet and the speed of the clothing. By using the speed of the jet at the entry into the clothing at a given pressure of the jet at the nozzle outlet and entry into the clothing, the water permeability of the moving clothing is determined and/or at least one surface property of the moving clothing is determined. A corresponding apparatus is also specified.

25 Claims, 1 Drawing Sheet

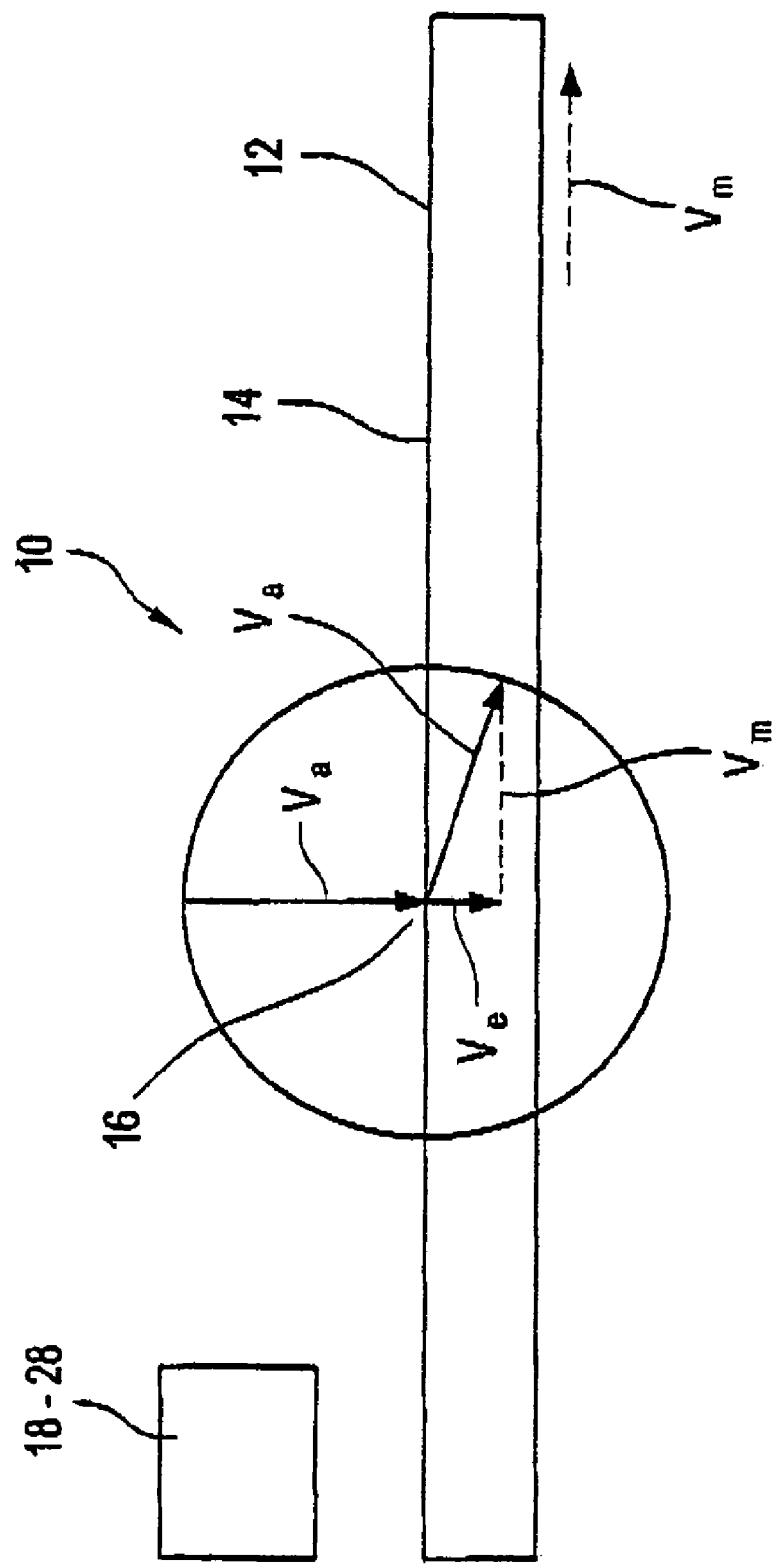

METHOD AND APPARATUS FOR DETERMINING AT LEAST ONE PROPERTY OF MOVING CLOTHING IN A PAPER MACHINE

BACKGROUND OF THE INVENTION

1. Field of the Invention

The present invention relates to a method and an apparatus for determining at least one property of moving clothing of a machine for producing and/or treating a material web, in particular a paper or board web.

2. Description of the Related Art

Methods and apparatuses for determining the water permeability of water permeable clothing or fabrics in a papermaking machine by way of a nozzle device aimed at the surface of the clothing are disclosed by the documents DE 199 17 553 A1 and U.S. Pat. No. 4,880,499, for example. According to DE 199 17 553 A1, while maintaining a constant water flow, the pressure in the nozzle is measured, the water flow being acted on optionally with a gas, in particular air. On the other hand, in U.S. Pat. No. 4,880,499, it is proposed to measure the flow through the nozzle device while maintaining a constant pressure in a range from 2 to 1000 kPa within the nozzle device. The pressure or the flow is then used as a measured variable proportional to the permeability.

Although both methods and apparatuses are suitable for determining the permeability of water permeable fabrics in the stationary state, in practice the fabrics are normally moved at speeds of up to 2200 m/min. If the water permeability is measured under the conditions just mentioned in one of the known methods, this leads to a highly distorted measured result, which permits only a few conclusions about the actual permeability. A comparable measurement at different fabric speeds is barely possible.

What is needed in the art is a method and apparatus for a measurement of water permeability that is independent of the speed of the clothing.

SUMMARY OF THE INVENTION

The present invention provides a measurement of the water permeability of the water-permeable clothing that is independent of the speed of the clothing relative to the measuring apparatus or nozzle to be possible.

The invention comprises, in one form thereof, a method for determining at least one property of moving clothing of a machine for producing and/or treating a material web, in particular a paper or board web, having the following steps: arranging a nozzle opposite the surface of the moving clothing; producing a jet acting on the clothing by way of the nozzle contacting the moving clothing; measuring a variable representative of the flow through the nozzle; measuring a variable representative of the pressure of the jet at the nozzle outlet; determining the speed of the jet at the nozzle outlet from the nozzle flow and the free surface of the jet medium at the point of contact with the clothing; and determining the speed of the jet at the entry into the clothing from the speed of the jet at the nozzle outlet and the speed of the clothing. By using the speed of the jet at the entry into the clothing at a given pressure of the jet at the nozzle outlet and entry into the clothing, the water permeability of the moving clothing is determined and/or at least one surface property of the moving clothing is determined. It is preferable if at least two different speeds of the jet at the entry into the clothing are set one after another and the measured and calculated results are compared with one other.

On the basis of this presently inventive configuration of the method, a measurement of the water permeability of the water-permeable fabric is possible, independent of the speed of the clothing relative to the nozzle.

Furthermore, by way of suitable variations of the measurement parameters, different properties such as the permeability and surface properties of the clothing can be determined. The measured and calculated results permit specific cleaning or conditioning or else lifetime analysis of the clothing. Service lives of the clothing can be optimized in this way, and clothing changes can be planned; therefore, unplanned stoppages of the papermaking machine are avoided.

When determining a respective property of the moving clothing, the starting point is expediently the respective speed vectors. In this case, the vectors of the speed of the jet at the nozzle outlet and the speed of the jet at the entry into the clothing in each case run at right angles to the surface of the clothing that is acted on and at right angles to the speed of the clothing, respectively.

The jet therefore emerges from the nozzle outlet at a specific speed and strikes the clothing, where it is deflected. Following the deflection, the jet has two components, of which one corresponds to the speed of the jet at the entry into the clothing and the other corresponds to the speed of the clothing. The speed of the jet at the nozzle outlet is given by the known nozzle flow and the free surface of the water at the point of contact with the clothing. From the speed of the jet at the nozzle outlet and the speed of the clothing, via the given geometric relationships, that is to say via the following relationship, the speed of the jet at the entry into the clothing can be determined:

$$v_e = \sqrt{v_a^2 - v_m^2}$$

where $v_a$=speed of the jet at the nozzle outlet
$v_e$=speed of the jet at the entry into the clothing
$v_m$=speed of the clothing.

The angle between $v_e$ and $v_a$ can be between 0° and 90°, at an angle of 90° the speed $v_m$ of the clothing being greater than or equal to the speed $v_a$ of the jet at the nozzle outlet. In this case, the clothing simply carries the jet with it. It is therefore only surface properties of the clothing which are measured ($v_e = 0$).

If the speed $v_a$ of the jet at the nozzle outlet is greater than the speed $v_m$ of the clothing, then the jet penetrates into the clothing at the point of contact with the entry speed $v_e$. Since the jet immediately spreads out within the clothing, the geometric relationship cited above applies only close to the surface of the clothing. An entry speed $v_e$ is definitely present, however, that is to say the jet passes through the surface of the clothing.

The greater the entry speed $v_e$ as compared with the speed $v_a$ of the jet at the nozzle outlet, the more intensely or the deeper will the jet penetrate into the clothing before it spreads out. It is of particular advantage if the jet penetrates into the clothing before it spreads out; it will also penetrate deeper.

It is especially of particular advantage if at least two different speeds of the jet at the nozzle outlet and/or at least two different speeds of the jet at the entry into the clothing are set one after another and the measured and calculated results are compared with one another. From the values, results and/or comparisons determined, it is possible in particular to draw conclusions about at least one permeability and/or surface property of the clothing.

For measurements at one speed $v_e$ of the jet at the entry into the clothing greater than zero, the permeability can be determined or calculated. In this case, the permeability is a function of the pressure p of the jet at the nozzle outlet, of the flow through the nozzle and of the speed $v_m$ of the clothing. The higher the speed $v_a$ at the nozzle outlet, the greater also is the depth action of the permeability measurement. It is therefore possible to determine permeabilities with different depth effects. If a speed $v_e$ of the jet at the entry into the clothing is equal to zero, on the other hand, only surface properties of the clothing are registered.

In practical terms, even at a speed $v_e$ of the jet at the entry into the clothing equal to zero, the jet penetrates slightly into the clothing. In this case, the penetration depth corresponds at most to the thickness of the original jet. In view of the unavoidable spreading, the actual penetration depth is lower. In addition, it is necessary to take account of the fact that the surface of the clothing is rough and can carry a certain amount of water with it without any penetration taking place. If the speed $v_a$ of the jet at the nozzle outlet becomes still lower, that is to say $v_a < v_m$, then the possibility of limited penetration of the jet decreases further.

It follows from this, moreover, that for an application of the invention to high speed papermaking machines, pressures are required which are far greater than 6 bar. At 6 bar (60 m water column), the speed $v_a$ of the jet at the nozzle outlet is only $\sqrt{2 \ast g \ast h} = 2100$ m/min, which is still of the order of magnitude of the speed $v_m$ of the clothing.

According to a preferred practical configuration of the method according to the present invention, the pressure of the jet at the nozzle outlet is therefore selected to be greater than 6 bar.

A further approach to registering the depth effect separately compares at least two operating points resulting at different pressures p of the jet at the nozzle outlet with one another. In this case, the different pressures of the jet at the nozzle outlet in each case are preferably selected to be greater than 6 bar. Here, for example, about 10 bar can be selected for one operating point and about 20 bar for the other operating point.

Via the relevant geometric relationships, the following are then again obtained:

$$v_{e1} = \sqrt{v_{a1}^2 - v_m^2}$$

$$v_{e2} = \sqrt{v_{a2}^2 - v_m^2}$$

$$\Delta v_{e2} = v_{e2} - v_{e1}$$

$$\Delta p = 20 \text{ bar} - 10 \text{ bar} = 10 \text{ bar}$$

Depth permeability = $\Delta v_e / \Delta p$.

As a result, the distortion of the measured result by surface effects, which can still be dominant at lower pressures, is also reduced. The moving clothing can be formed in particular by a fabric band, for example by a felt. The jet medium preferably contains water.

According to the present invention, an apparatus for determining at least one property of moving clothing of a machine for producing and/or treating a material web, in particular a paper or board web, in particular for carrying out the aforementioned method, comprises a nozzle aimed at the surface of the moving clothing and touching the latter for producing a jet acting on the clothing, elements for measuring a variable representative of the flow through the nozzle, elements for measuring a variable representative of the pressure of the jet at the nozzle outlet, elements for determining the speed of the jet at the nozzle outlet from the nozzle flow and from the free surface of the jet medium at the point of contact with the clothing, and elements for determining the speed of the jet at the entry into the clothing from the speed of the jet at the nozzle outlet and the speed of the clothing. The present invention also includes elements for determining the water permeability of the moving clothing by using the speed of the jet at the entry into the clothing at a given pressure of the jet at the nozzle outlet and entry into the clothing and/or for determining at least one surface property of the moving clothing.

Preferred embodiments of the apparatus according to the present invention are specified in the dependent claims.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawing, wherein:

The sole drawing is a schematic view of an apparatus for determining at least one property of moving clothing of a machine for producing and/or treating a material web, which can be in particular a paper or board web.

Corresponding reference characters indicate corresponding parts throughout the several views. The exemplification set out herein illustrate one preferred embodiment of the invention, in one form, and such exemplification is not to be construed as limiting the scope of the invention in any manner.

DETAILED DESCRIPTION OF THE INVENTION

Referring now to the sole drawing, there is shown an apparatus 10 which generally includes a nozzle 16 which is aimed at the surface 14 of the moving clothing 12 and touches the latter in order to produce a jet acting on the clothing 12.

Apparatus 10 moreover includes elements 18, merely indicated schematically here, for measuring a variable representative of the flow through nozzle 16, elements 20 for measuring a variable representative of the pressure p of the jet at the nozzle outlet, elements 22 for determining the speed $v_a$ of the jet at the nozzle outlet from the nozzle flow and from the free surface of the jet medium at the point of contact with the clothing 12, elements 24 for determining the speed $v_e$ of the jet at the entry into clothing 12 from the speed $v_a$ of the jet at the nozzle outlet and from the speed $v_m$ of clothing 12, and also elements 26, 28 for determining the water permeability of the moving clothing 12 by using the speed $v_e$ of the jet at the entry into clothing 12 at a given pressure p of the jet at the nozzle outlet and entry into clothing 12 and/or for determining at least one surface property of moving clothing 12.

Use is therefore made of a measuring instrument having nozzle 16 which slides with contact over clothing 12. Clothing 12 can be, for example, a fabric band and in particular a felt or the like. The flow through nozzle 16 and the pressure of the jet which is forced into clothing 12 are registered or calculated from other indirect variables.

The starting point here is a definition of the permeability as the speed $v_e$ with which the jet enters the clothing at a given entry pressure. The jet medium can in particular contain water or consist of water.

For the permeability, starting from the specified definition, the following relationship is therefore true:

$P_{erm} = v_e/p$, where $P_{erm}$ = permeability $v_e$ = speed of the jet at the entry into the clothing p = pressure of the jet at the nozzle outlet.

In addition, the respective speed vectors are used as a starting point, it again being true that:

$v_a$ = speed of the jet at the nozzle outlet $v_e$ = speed of the jet at the entry into the clothing $v_m$ = speed of the clothing.

The jet therefore emerges from nozzle 16 at the speed $v_a$ and strikes clothing 12. It is deflected there. Following the deflection, the jet has two components, namely the speed $v_m$ of clothing 12 and the speed $v_e$ of the jet at the entry into clothing 12.

The speed $v_a$ of the jet at the nozzle outlet is known from the nozzle flow and the free surface of the water at the point of contact with clothing 12. From the speed $v_a$ of the jet at the nozzle outlet and the speed $v_m$ of clothing 12, the speed $v_e$ of the jet at the entry into clothing 12 can be determined from the following geometric relationship:

$v_e = \sqrt{v_a^2 - v_m^2}$

The angle between the speed $v_e$ of the jet at the entry into the clothing and the speed $v_a$ of the jet at the nozzle outlet can be between 0° and 90°. An angle of 90° results when the speed $v_m$ of clothing 12 is greater than or equal to the speed $v_a$ of the jet at the nozzle outlet. The clothing then simply carries the jet with it. In this case, only surface properties of clothing 12 will be measured ($v_e=0$).

If the speed $v_a$ of the jet at the nozzle outlet is greater than the speed $v_m$ of clothing 12, the jet penetrates into clothing 12 at the entry speed $v_e$ at the point of contact. Since the jet immediately spreads out within clothing 12, the specified geometric relationship only applies close to the surface of clothing 12. However, a penetration depth or entry speed $v_e$ is definitely present. The jet passes through the surface of clothing 12.

The greater the speed $v_e$ of the jet at the entry into clothing 12 as compared with the speed $v_a$ of the jet at the nozzle outlet, the more intensely and correspondingly deeper will the jet penetrate into clothing 12 before it spreads out.

It is of particular advantage if two successive different nozzle outlet speeds $v_a$ and/or at least two different speeds $v_e$ of the jet at the entry into clothing 12 are selected and the measured and calculated results are compared with one another.

For measurements at a speed $v_e$ of the jet at the entry into clothing 12 greater than zero, the permeability can be calculated. In this case, this permeability is a function of the pressure p of the jet at the nozzle outlet, of the flow through nozzle 16 and of the speed $v_m$ of clothing 12. The higher the speed $v_a$ of the jet at the nozzle outlet, the greater is also the depth action of the permeability measurement or determination. It is therefore possible to determine the permeability with different depth effects. On the other hand, with a speed $v_e=0$, only surface properties of clothing 12 are registered.

In practical terms, even at a speed $v_e=0$ of the jet at the entry into clothing 12, the jet penetrates slightly into clothing 12. In this case, the penetration depth corresponds at most to the thickness of the original jet. In view of the unavoidable spreading, the actual penetration depth is lower, however. In addition, it is necessary to take account of the fact that the surface of clothing 12 is rough and can also carry a certain amount of water with it without any penetration taking place. If the speed of the jet becomes still lower, that is to say $v_a < v_m$, then the possibility of limited penetration of the jet decreases further.

It follows from this, moreover, that for the application of the presently inventive solution to high speed papermaking machines, pressures are required which are far greater than 6 bar. At 6 bar (60 m water column), the speed $v_a$ of the jet at the nozzle outlet is only $\sqrt{2*g*h}=2100$ m/min, which is still of the order of magnitude of the speed $v_m$ of clothing 12.

A further approach to registering the depth effect separately compares with each other at least two operating points of the measuring instrument or of apparatus 10 at relatively high pressures. For example, 10 bar can be selected for one operating point and 20 bar for the other operating point. Via the geometric relationship, the following are then obtained:

$v_{e1} = \sqrt{v_{a1}^2 - v_m^2}$ $v_{e2} = \sqrt{v_{a2}^2 - v_m^2}$ $\Delta v_e = v_{e2} - v_{e1}$ $\Delta p = 20$ bar $- 10$ bar $= 10$ bar Depth permeability = $\Delta v_e / \Delta p$.

As a result, the distortion of the measured result by surface effects, which can still be dominant at lower pressures, is also correspondingly reduced.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

List of Designations

10 Apparatus
12 Clothing, fabric band, felt
14 Surface of the clothing
16 Nozzle
18 Elements for measuring flow
20 Elements for measuring pressure
22 Elements for determining the jet exit speed
24 Elements for determining the jet entry speed
26 Elements for determining the water permeability
28 Elements for determining at least one surface property

What is claimed is:

1. A method for determining at least one property of a moving clothing of a machine for at least one of producing and treating a fiber material web, comprising the steps of:
   arranging a nozzle opposite a surface of the moving clothing;
   producing a jet acting on the moving clothing by way of said nozzle contacting the moving clothing;

measuring a variable representative of a nozzle flow through said nozzle;

measuring a variable representative of a pressure of said jet at an outlet of said nozzle;

determining a speed of said jet at said nozzle outlet from said nozzle flow and a free surface of a jet medium at a point of contact with said moving clothing;

determining a speed of said jet at an entry into the moving clothing from said speed of said jet at said nozzle outlet and a speed of the moving clothing;

using said speed of said jet at said entry into the moving clothing at a given said pressure of said jet at said nozzle outlet and said entry into the moving clothing to determine at least one of a water permeability of the moving clothing and at least one surface property of the moving clothing.

2. The method of claim 1, wherein the fiber material web is one of a paper web and a board web.

3. The method of claim 1, further including the steps of setting a plurality of different speeds of said jet at said entry into the moving clothing one after another and comparing a plurality of measured and calculated results with each other resulting from said setting step.

4. The method of claim 3, further including the step of drawing at least one conclusion about said at least one of said water permeability of the moving clothing and said at least one surface property of the moving clothing from at least one of a plurality of values, said plurality of measured and calculated results and a plurality of comparisons from said comparing step.

5. The method of claim 1, wherein when determining said at least one of said water permeability of the moving clothing and said at least one surface property of the moving clothing a starting point is a plurality of respective speed vectors.

6. The method of claim 5, wherein said plurality of respective speed vectors includes a vector of said speed of said jet at said nozzle outlet which is at a right angle to a surface of the moving clothing that is acted on and is also at a right angle to a speed of the moving clothing, and a vector of said speed of said jet at said entry into the moving clothing which is at a right angle to a surface of the moving clothing that is acted on and is also at a right angle to a speed of the moving clothing.

7. The method of claim 1, wherein said pressure of said jet at said nozzle outlet is greater than 6 bar.

8. The method of claim 1, further including the step of comparing a plurality of operating points resulting at a plurality of different pressures of said jet at said nozzle outlet.

9. The method of claim 8, further including the step of selecting all of said plurality of different pressures of said jet at said nozzle outlet to be greater than 6 bar.

10. The method of claim 8, further including the step selecting one of said plurality of different pressures to be about 10 bar for one of said plurality of operating points and another of said plurality of different pressures to be about 20 bar for another of said plurality of operating points.

11. The method of claim 1, further including the step of forming the moving clothing by a fabric band.

12. The method of claim 1, further including the step of forming the moving clothing by a felt.

13. The method of claim 1, further including a jet medium associated with said jet, said jet medium containing water.

14. An apparatus for determining at least one property of a moving clothing of a machine for at least one of producing and treating a fiber material web, comprising:

a nozzle aimed at a surface of the moving clothing and touching the moving clothing for producing a jet acting on the clothing, said nozzle including a nozzle outlet;

means for measuring a variable representative of a flow through said nozzle;

means for measuring a variable representative of a pressure of said jet at said nozzle outlet;

means for determining a speed of said jet at said nozzle outlet from a nozzle flow and from a free surface of a jet medium at a point of contact with the moving clothing;

means for determining a speed of said jet at an entry into the moving clothing from said speed of said jet at said nozzle outlet and a speed of the moving clothing; and means for at least one of determining a water permeability of the moving clothing by using said speed of said jet at said entry into the moving clothing at a given said pressure of said jet at said nozzle outlet and said entry into the moving clothing and determining at least one surface property of the moving clothing.

15. The apparatus of claim 14, wherein the fiber material web is one of a paper web and a board web.

16. The apparatus of claim 14, further including at least two different speeds of said jet at said entry into the moving clothing being set one after another, a plurality of measured and calculated results associated with said at least two different speeds being compared with one another.

17. The apparatus of claim 14, further including a plurality of respective speed vectors associated with said speed of said jet at said nozzle outlet, said speed of said jet at an entry into the moving clothing and said speed of the moving clothing, a respective property of the moving clothing being determined on a basis of said plurality of respective speed vectors.

18. The apparatus of claim 17, further including a vector of said speed of said jet at said nozzle outlet which is at a right angle to a surface of the moving clothing and is also at a right angle to said speed of the clothing, and a vector of said speed of said jet at an entry into the moving clothing which is at a right angle to a surface of the moving clothing and is also at a right angle to said speed of the clothing.

19. The apparatus of claim 14, wherein said pressure of said jet at said nozzle outlet is greater than 6 bar.

20. The apparatus of claim 14, further including at least two operating points resulting at a plurality of different pressures of said jet at said nozzle outlet, said at least two operating points being compared with one another.

21. The apparatus of claim 20, wherein all said plurality of different pressures of said jet at said nozzle outlet are greater than 6 bar.

22. The apparatus of claim 21, wherein one of said plurality of different pressures is about 10 bar for one of said plurality of operating points, another of said plurality of different pressures is about 20 bar for another of said plurality of operating points.

23. The apparatus of claim 14, wherein the moving clothing is formed by a fabric band.

24. The apparatus of claim 14, wherein the moving clothing is formed by a felt.

25. The apparatus of claim 14, further including a jet medium associated with said jet, said jet medium containing water.

* * * * *

UNITED STATES PATENT AND TRADEMARK OFFICE
CERTIFICATE OF CORRECTION

PATENT NO. : 6,971,261 B2
APPLICATION NO. : 10/943656
DATED : December 6, 2005
INVENTOR(S) : Ischdonat et al.

It is certified that error appears in the above-identified patent and that said Letters Patent is hereby corrected as shown below:

Column 3,
Line 50, delete "$\Delta v_{e2}$", and substitute -- $\Delta v_e$ --.

Signed and Sealed this

Twentieth Day of June, 2006

JON W. DUDAS
*Director of the United States Patent and Trademark Office*